United States Patent
Ashihara et al.

(10) Patent No.: US 12,186,088 B2
(45) Date of Patent: Jan. 7, 2025

(54) RECORDING DEVICE, RECORDING METHOD, AND PROGRAM

(71) Applicants: NATIONAL UNIVERSITY CORPORATION SHIGA UNIVERSITY OF MEDICAL SCIENCE, Otsu (JP); NIHON KOHDEN CORPORATION, Tokyo (JP); Takeshi TSUCHIYA, Kumamoto (JP)

(72) Inventors: Takashi Ashihara, Otsu (JP); Koji Takizawa, Tokorozawa (JP); Takeshi Tsuchiya, Kumamoto (JP)

(73) Assignees: NATIONAL UNIVERSITY CORPORATION SHIGA UNIVERSITY OF MEDICAL SCIENCE, Shiga (JP); NIHON KOHDEN CORPORATION, Tokyo (JP); Takeshi Tsuchiya, Kumamoto (JP)

( * ) Notice: Subject to any disclaimer, the term of this patent is extended or adjusted under 35 U.S.C. 154(b) by 704 days.

(21) Appl. No.: 17/425,459

(22) PCT Filed: Jan. 14, 2020

(86) PCT No.: PCT/JP2020/000891
§ 371 (c)(1),
(2) Date: Jul. 23, 2021

(87) PCT Pub. No.: WO2020/153175
PCT Pub. Date: Jul. 30, 2020

(65) Prior Publication Data
US 2022/0087590 A1 Mar. 24, 2022

(30) Foreign Application Priority Data
Jan. 25, 2019 (JP) .................. 2019-011333

(51) Int. Cl.
*A61B 5/333* (2021.01)
*A61B 5/00* (2006.01)
(Continued)

(52) U.S. Cl.
CPC .............. *A61B 5/333* (2021.01); *A61B 5/346* (2021.01); *G16H 40/63* (2018.01); *A61B 5/287* (2021.01);
(Continued)

(58) Field of Classification Search
CPC ........ A61B 5/333; A61B 5/346; A61B 5/7203
See application file for complete search history.

(56) References Cited

U.S. PATENT DOCUMENTS

| 6,360,121 B1 | 3/2002 | Shoda et al. |
| 2010/0234746 A1 | 9/2010 | Sebelius |

(Continued)

FOREIGN PATENT DOCUMENTS

| CN | 1829471 A | 9/2006 |
| CN | 101384214 A | 3/2009 |

(Continued)

OTHER PUBLICATIONS

Stevenson et al., "Recording Techniques for Clinical Electrophysiology". Techniques and Technology, J Cardiovasc Electrophysiol, vol. 16, Sep. 2005, (6 total pages).

(Continued)

*Primary Examiner* — Paula J Stice
(74) *Attorney, Agent, or Firm* — Sughrue Mion, PLLC (57) ABSTRACT

A recording device includes an acquisition unit configured to acquire vital signs through a sensor device having a plurality of electrodes, a recording unit configured to record a bipolar potential of a main channel which is defined by combining the plurality of electrodes, using the vital signs, an addition unit configured to add a mark to each waveform plotted (Continued)

based on variation of the bipolar potential over time, at a predetermined position on a time axis, and an adjusting unit configured to adjust a position of the mark added to each waveform. The adjusting unit is configured to adjust the position of the mark added to the bipolar potential of the main channel, based on bipolar potentials of reference channels including electrodes included in the main channel.

9 Claims, 7 Drawing Sheets

(51) Int. Cl.
*A61B 5/346* (2021.01)
*G16H 40/63* (2018.01)
*A61B 5/287* (2021.01)

(52) U.S. Cl.
CPC ..... *A61B 5/7203* (2013.01); *A61B 2560/0475* (2013.01)

(56) References Cited

U.S. PATENT DOCUMENTS

| | | | |
|---|---|---|---|
| 2012/0184863 | A1 | 7/2012 | Harlev et al. |
| 2012/0184864 | A1 | 7/2012 | Harlev et al. |
| 2012/0184865 | A1 | 7/2012 | Harlev et al. |
| 2013/0102871 | A1 | 4/2013 | Sebelius et al. |
| 2013/0109945 | A1 | 5/2013 | Harlev et al. |
| 2014/0349332 | A1 | 11/2014 | Yasuda et al. |
| 2015/0032014 | A1 | 1/2015 | Ghosh |
| 2015/0112178 | A1 | 4/2015 | Harlev et al. |
| 2015/0238102 | A1 | 8/2015 | Rubinstein et al. |
| 2016/0051160 | A1 | 2/2016 | Harlev et al. |
| 2016/0067498 | A1 | 3/2016 | Ghosh |
| 2017/0042436 | A1 | 2/2017 | Harlev et al. |
| 2017/0143976 | A1 | 5/2017 | Ghosh |
| 2017/0319088 | A1 | 11/2017 | George et al. |

FOREIGN PATENT DOCUMENTS

| | | |
|---|---|---|
| CN | 103327887 A | 9/2013 |
| CN | 104856668 A | 8/2015 |
| CN | 105578955 A | 5/2016 |
| CN | 109069049 A | 12/2018 |
| EP | 2 912 997 A1 | 2/2015 |
| JP | 2001-37730 A | 2/2001 |
| JP | 2013-523345 A | 6/2013 |
| JP | 2014-502556 A | 2/2014 |
| JP | 2015-160138 A | 9/2015 |
| WO | 2004/110241 A2 | 12/2004 |
| WO | 2011/127211 A2 | 10/2011 |

OTHER PUBLICATIONS

Namba et al., "Identification of local myocardial repolarization time by bipolar electrode potential," Elsevier, Journal of Electrocardiology 40, Jun. 18, 2007, (6 total pages).

Nakagawa et al., "Rapid High Resolution Electroanatomical Mapping Evaluation of a New System in a Canine Atrial Linear Lesion Model," Circ Arrhythm Electrophysiol, Feb. 27, 2012, (8 pages).

Ciaccio et al., "Multichannel Data Acquisition System for Mapping the Electrical Activity of the Heart," Pace—Pacing and Clinical Electrophysiology., vol. 28, No. 8, Aug. 1, 2005, (13 pages).

Masuda et al. "The identification of conduction gaps after pulmonary vein isolation using a new electroanatomic mapping system", CrossMark, Heart Rhythm, vol. 14, No. 11, Nov. 1, 2017, (9 pages).

International Search Report (PCT/ISA/210) dated Mar. 16, 2020 issued by the International Searching Authority in International Application No. PCT/JP2020/000891.

Written Opinion (PCT/ISA/237) dated Mar. 16, 2020 issued by the International Searching Authority in International Application No. PCT/JP2020/000891.

Communication dated Aug. 2, 2022 issued by the Japanese Intellectual Property Office in counterpart Japanese Application No. 2019-011333.

Office Action dated Dec. 26, 2023, issued by the China National Intellectual Property Administration in counterpart Chinese Patent Application No. 202080010785.4.

RECORDING DEVICE, RECORDING METHOD, AND PROGRAM

TECHNICAL FIELD

The presently disclosed subject matter relates to a recording device, a recording method, and a program for recording bipolar potentials.

BACKGROUND ART

In Non-Patent Literature 1 and Non-Patent Literature 2, as some of methods of recording potentials in hearts, an unipolar potential recording method and a bipolar potential recording method using electrode catheters brought into contact with heart walls by inserting them into hearts or in any other way are disclosed. The unipolar potential recording method has an advantage that it is easy to reflect the polarities or waveforms of local potentials, but the unipolar method has a disadvantage that the potentials of comparatively wide ranges apart from electrodes might be recorded, whereby wrong local excitation timings might be erroneously recognized. Meanwhile, the bipolar potential recording method uses the difference between two unipolar potential records. Therefore, the bipolar method has a disadvantage that it is difficult for the polarities or waveforms of local potentials to be reflected. However, the bipolar method has an advantage that it is possible to more accurately record the excitation timings of local spots.

In order to capture excitation propagation in hearts and use it for diagnosis and treatment of arrhythmia, a new heart excitation analysis technique capable of remedying the disadvantages of the two kinds of potential recording methods is required.

CITATION LIST

Non Patent Literature

NPL 1: Stevenson W G, Soejima K: Recording techniques for clinical electro-physiology. J Cardiovasc Electrophysiol 2005; 16: 1017-1022.

NPL 2: Namba T. Todo T, Yao T, Ashihara T, Haraguchi R. Nakazawa K, Ikeda T, Ohe T: Identification of local myocardial repolarization time by bipolar electrode potential. J Electrocardiol 2007; 40(Suppl.6): S97-S102.

SUMMARY OF INVENTION

Technical Problem

In fact, sometimes, when analyzing a heart by the bipolar potential recording method of the related art, it is impossible to accurately record potential waveforms due to noise or a failure in contact of any one electrode of two unipolar electrodes constituting a bipolar electrode with the heart wall. Also, in the case where the arrangement of two unipolar electrodes constituting a bipolar electrode is perpendicular to the propagation direction of excitation, since the waveforms which are recorded by the two unipolar electrodes become the same, the waveform of the bipolar potential which is the difference between them disappears, and the accuracy of analysis decreases.

Therefore, an object of the presently disclosed subject matter is to provide a recording device, a recording method, and a program for making it possible to remedy the disadvantage of a mark distribution chart recorded by the bipolar potential recording method using a multi-electrode catheter brought into contact with a heart wall and improve the accuracy of analysis of heart excitation.

Solution to Problem

In order to achieve the above object, a recording device of the presently disclosed subject matter includes: an acquisition unit configured to acquire vital signs through a sensor device having a plurality of electrodes; a recording unit configured to record a bipolar potential of a main channel which is defined by combining the plurality of electrodes, using the vital signs; an addition unit configured to add a mark to each waveform plotted based on variation of the bipolar potential over time, at a predetermined position on a time axis; and an adjusting unit configured to adjust a position of the mark added to each waveform. The adjusting unit is configured to adjust the position of the mark added to the bipolar potential of the main channel, based on bipolar potentials of reference channels including electrodes included in the main channel.

According to the above-described configuration, the reference channels am defined as including the electrodes included in the main channel, and the bipolar potentials of the reference channels and the bipolar potential of the main channel have a certain relevance. Therefore, for example, even though the position of the mark added to each waveform by the addition unit is influenced by noise, the adjusting unit can adjust the position on the time axis of the mark included in the bipolar potential of the main channel, using the bipolar potentials of the reference channels. As described above, the position of the mark once added can be adjusted, whereby it is possible to improve the accuracy of analysis using a bipolar potential mark distribution chart.

Moreover, a recording method of the presently disclosed subject matter includes: acquiring vital signs through a sensor device having a plurality of electrodes; recording a bipolar potential of a main channel which is defined by combining the plurality of electrodes, using the vital signs; adding a mark to each waveform plotted based on variation of the bipolar potential over time, at a predetermined position on the time axis; and adjusting a position of the mark added to each waveform. The adjusting includes, based on bipolar potentials of reference channels including electrodes included in the main channel, adjusting the position of the mark added to the bipolar potential of the main channel.

According to the above-described method, similarly to or same as the above-described recording device, it is possible to improve the accuracy of analysis using a bipolar potential mark distribution chart.

Moreover, a program of the presently disclosed subject matter makes a computer to execute a process. The process includes: acquiring vital signs through a sensor device having a plurality of electrodes; recording a bipolar potential of a main channel which is defined by combining the plurality of electrodes, using the vital signs; adding a mark to each waveform plotted based on variation of the bipolar potential over time, at a predetermined position on the time axis; and adjusting a position of the mark added to each waveform. The adjusting includes, based on bipolar potentials of reference channels including electrodes included in the main channel, adjusting the position of the mark added to the bipolar potential of the main channel.

According to the above-described program, similarly to or same as the above-described recording device, it is possible to improve the accuracy of analysis using a bipolar potential mark distribution chart even from the cardiac electrophysiological viewpoint.

According to the presently disclosed subject matter, it is possible to provide a recording device, a recording method, and a program capable of improving the accuracy of analysis using a bipolar potential mark distribution chart.

DESCRIPTION OF EMBODIMENTS

Hereinafter, an embodiment of the presently disclosed subject matter will be described with reference to the drawings.

Figure 1:
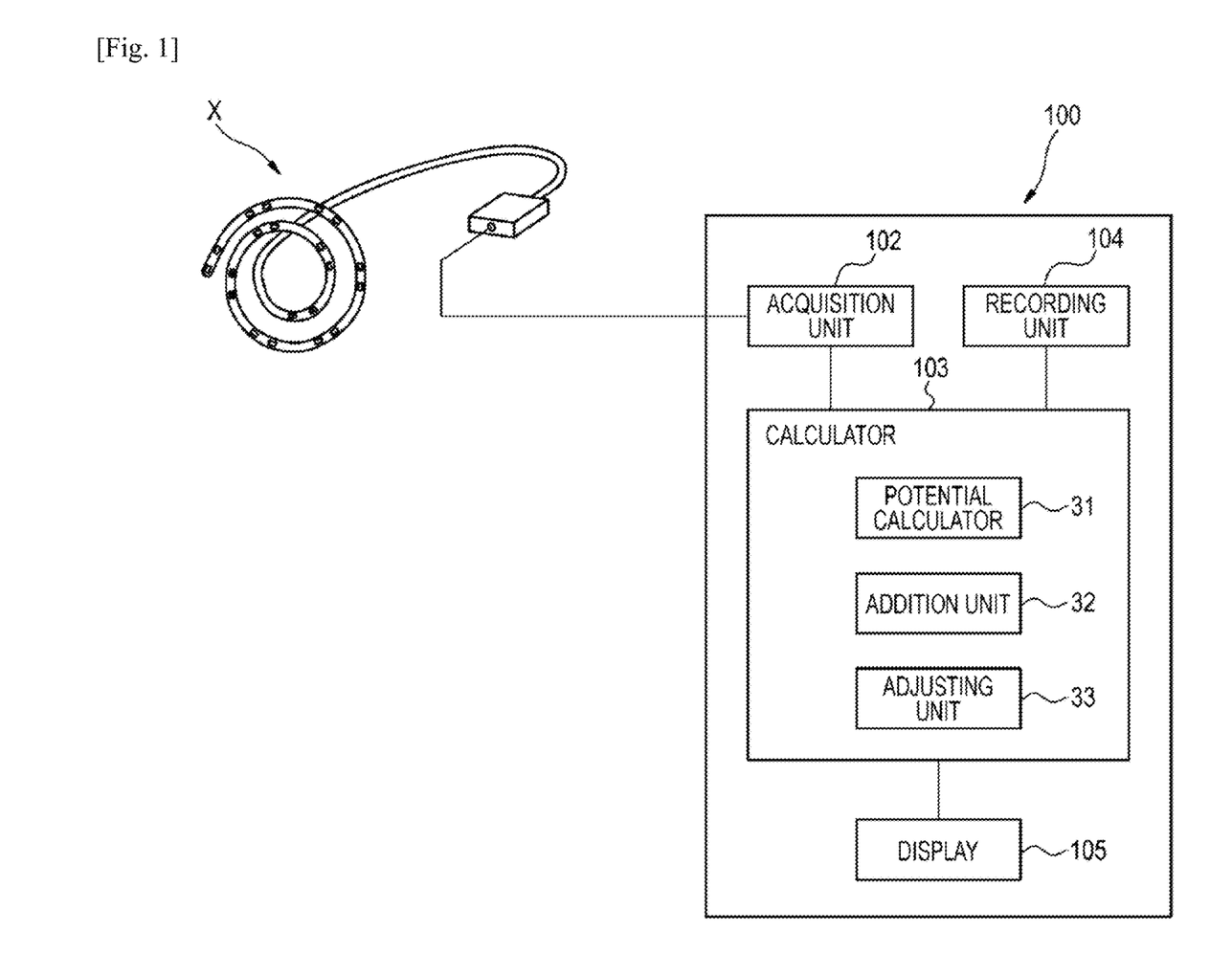
FIG. 1 is a block diagram illustrating the configuration of a recording device according to an embodiment.

FIG. 1 is a block diagram illustrating the configuration of a recording device 100 according to the embodiment of the presently disclosed subject matter. As illustrated in FIG. 1, the recording device 100 can include an acquisition unit 102, a calculator 103, a recording unit 104, and a display 105. The acquisition unit 102, the recording unit 104, and the display 105 are connected to the calculator 103 such that communication is possible. The recording device 100 can be used, for example, as a device for performing a function of the recording device 100. The above-mentioned individual functional units are realized by cooperation of hardware composed of one or more CPUs (Central Processing Units), one or more memories, and so on.

The acquisition unit 102 acquires vital signs of a subject detected by a sensor device. The sensor device is configured, for example, by a multi-electrode catheter X having a plurality of electrodes. The multi-electrode catheter X can be inserted into the heart of a subject, and detect, for example, the intracardiac electrocardiogram (ECG) in an atrium. After being inserted, the multi-electrode catheter X can change the shape to, for example, a spiral shape as illustrated in FIG. 1, in the heart.

The calculator 103 performs calculating processes for various analyzing processes to be performed in the subsequent stages, on the intracardiac ECG acquired by the acquisition unit 102. The calculator 103 can include a potential calculator 31, an addition unit 32, and an adjusting unit 33.

The potential calculator 31 calculates the potential difference between each of predetermined pairs of electrodes on the basis of electric signals of the individual electrodes acquired by the acquisition unit 102, and generates waveforms to be plotted, according to the potential differences. Hereinafter, the potential difference between two electrodes will be referred to as a bipolar potential, and the waveform of a potential difference which is plotted according to a bipolar potential will be referred to as a bipolar potential waveform. Also, a combination of two predetermined electrodes will be referred to as a channel. The bipolar potentials and bipolar potential waveforms of the channels generated are recorded in the recording unit 104.

The addition unit 32 adds one or more marks to the bipolar potential waveforms of the individual channels generated by the potential calculator 31 so as to be positioned at certain positions on the time axis. Here, the marks are also referred to as annotations (signs) indicating representative positions of the individual bipolar potential waveforms on the time axis. A criteria for adding marks can be appropriately set. For example, the position of each mark may be set such that the corresponding mark is added in the middle between two peaks of a bipolar potential waveform. Alternatively, each mark may be set at any other position, for example, on a rising or falling edge of a bipolar potential waveform. The position of each mark on the time axis is recorded in the recording unit 104 in association with a bipolar potential waveform.

The adjusting unit 33 adjusts the positions of the mark added to each bipolar potential waveform, on the basis of the positions of the marks added to the bipolar potential waveforms of other channels. Hereinafter, a channel on which adjustment is performed will be referred to as a main channel, and channels which are used for adjustment will be referred to as reference channels. The adjusted position of each mark on the time axis is recorded in the recording unit 104 in association with the corresponding bipolar potential waveform.

In the recording unit 104, as described above, data such as the bipolar potentials, the bipolar potential waveforms, the unadjusted positions of the individual marks on the time axis, and the adjusted positions of the individual marks on the time axis are recorded. The recording unit 104 may include a "MYOCARDIAL EXCITATION COMPLEMENTATION/VISUALIZATION APPARATUS AND MYOCARDIAL EXCITATION DETECTION APPARATUS" and "MYOCARDIAL EXCITATION DETERMINING APPARATUS" such as, for example, the apparatus described in U.S. Patent Publication Numbers 2018/0070844 and 2019/0076041, hereby incorporated by reference in their entireties.

On the display 105, for example, the bipolar potential waveforms of the individual channels having the initial marks added by the addition unit 32 are displayed. Also, on the display 105, the bipolar potential waveforms of the individual main channels having the marks at the positions adjusted by the adjusting unit 33 are displayed. Also, on the display 105, the bipolar potential waveforms of main channels with marks to be adjusted, and the bipolar potential waveforms of reference channels with marks to be used for the adjustment are displayed in parallel such that it is possible to compare them (see FIG. 3 for instance). The display 105 is configured with, for example, a touch panel type liquid crystal screen, and can display the above-mentioned display contents such that switching between the contents is possible.

Figure 2:
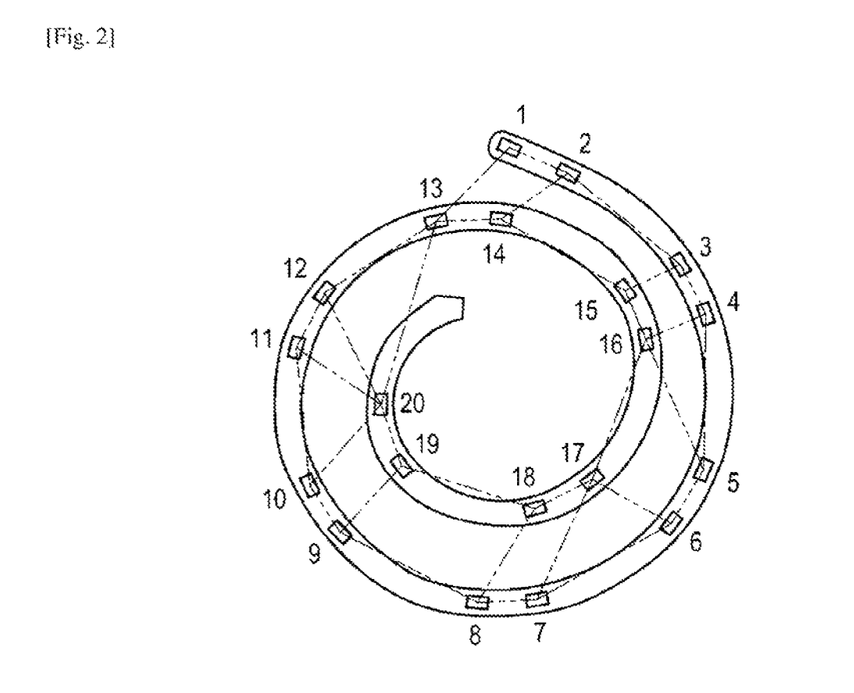
FIG. 2 illustrates an example of a sensor device.

FIG. 2 illustrates an example of the multi-electrode catheter X. As illustrated in FIG. 2, the multi-electrode catheter X has a plurality of electrodes (in the present example, twenty electrodes, i.e. an electrode 1 to an electrode 20) at the leading end part. The twenty electrodes (the electrode 1 to the electrode 20) are arranged at predetermined intervals along the longitudinal direction of the multi-electrode catheter X. The multi-electrode catheter X is inserted into a heart, and is placed so as to be in contact with the heart wall in a predetermined area inside an atrium while maintaining the shape in the spiral shape.

Channels which can be defined by predetermined combinations each of which composed of two electrodes of the electrode 1 to the electrode 20 of the multi-electrode catheter X are set. In the present example, as shown in Table 1, 32 channels CH 1 to CH 32 are set. Also, each of the channels, i.e. CH 1 to CH 32 which are set is configured by combining two neighboring electrodes of the twenty electrodes (the electrode 1 to the electrode 20), or by combining two electrodes disposed relatively closer to each other than other electrodes. For example, CH 1 is configured by the electrode 1 and the electrode 2. CH 2 is configured by the electrode 2 and the electrode 3. CH 20 is configure d by the electrode 1 and the electrode 13. CH 32 is configured by the electrode 13 and the electrode 20.

TABLE 1

| Channel | Electrode |
| --- | --- |
| CH 1 | 1-2 |
| CH 2 | 2-3 |
| CH 3 | 3-4 |
| CH 4 | 4-5 |
| CH 5 | 5-6 |
| CH 6 | 6-7 |
| CH 7 | 7-8 |
| CH 8 | 8-9 |
| CH 9 | 9-10 |
| CH 10 | 10-11 |
| CH 11 | 11-12 |
| CH 12 | 12-13 |
| CH 13 | 13-14 |
| CH 14 | 14-15 |
| CH 15 | 15-16 |
| CH 16 | 16-17 |
| CH 17 | 17-18 |
| CH 18 | 18-19 |
| CH 19 | 19-20 |
| CH 20 | 1-13 |
| CH 21 | 2-14 |
| CH 22 | 3-15 |
| CH 23 | 4-16 |
| CH 24 | 5-16 |
| CH 25 | 6-17 |
| CH 26 | 7-17 |
| CH 27 | 8-18 |
| CH 28 | 9-19 |
| CH 29 | 10-20 |
| CH 30 | 11-20 |
| CH 31 | 12-20 |
| CH 32 | 13-20 |

Figure 3:
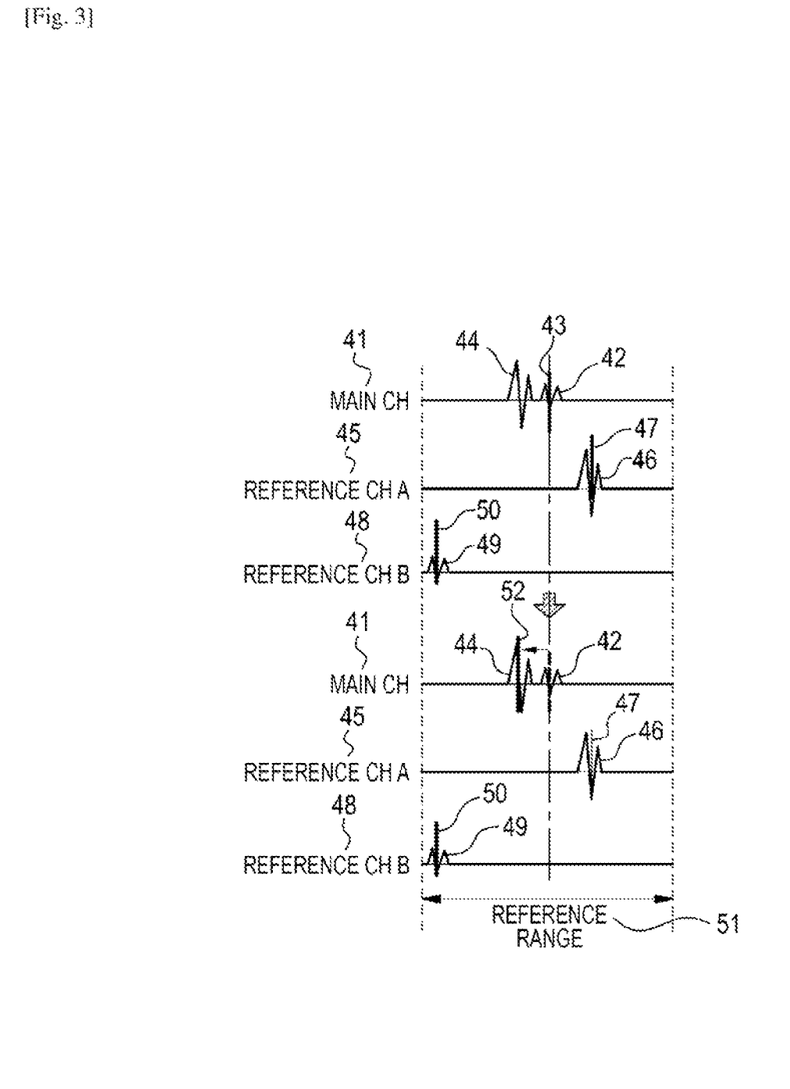
FIG. 3 is a view for explaining mark position adjustment.

FIG. 3 illustrates an example in which the positions of marks added to the bipolar potential waveforms of the main channels are adjusted on the basis of marks added to the bipolar potential waveforms of the reference channels. As illustrated in FIG. 3, in this example, with respect to the bipolar potential waveform of each main channel to be adjusted, two reference channels (a reference channel A and a reference channel B) are provided as channels to be used for the adjustment. With respect to each channel, at least two reference channels can be provided.

Adjustment of the position of a mark on the bipolar potential waveform of a main channel is performed on the basis of the positions of marks added to the bipolar potential waveforms of reference channels highly relevant to the main channel. As highly relevant reference channels, for example, channels which are composed of electrodes of the individual electrodes of the multi-electrode catheter X disposed close to the electrodes of the main channel are selected. Specifically, reference channels highly relevant to a main channel are, for example, channels each of which is composed of a combination of electrodes including one electrode of two electrodes constituting the main channel (as will be described below with reference to Table 2).

In the present example, each mark indicating the position of a bipolar potential waveform on the time axis is added in the middle between two peaks of the bipolar potential waveform. In a main channel 41 illustrated in FIG. 3, a mark 43 is added in the middle between two peaks of a bipolar potential waveform 42. Also, in a reference channel A 45, a mark 47 is added in the middle between two peaks of a bipolar potential waveform 46. In a reference channel B 48, a mark 50 is added in the middle between two peaks of a bipolar potential waveform 49.

By the way, in the main channel 41 illustrated in FIG. 3, two bipolar potential waveforms, each of which has two peaks (the bipolar potential waveform 42 and a bipolar potential waveform 44), are detected, and to one of them (in FIG. 3, the right one), i.e. the bipolar potential waveform 42, the mark 43 is added. For example, since the bipolar potential waveform 44 is included in the detection exclusion period in which waveform detection is not performed during the process in which the bipolar potential waveform on the front side on the time axis (in FIG. 3, the left side) is detected, addition of the mark 43 can be performed when the bipolar potential waveform 44 is excluded from waveforms which are objects of addition of the mark 43. However, in the case where a plurality of bipolar potential waveforms, each of which has two peaks like the main channel 41, am detected, for example, a bipolar potential waveform of them on the rear side on the time axis (in FIG. 3, the right side) may be estimated as a formal bipolar potential waveform, and a mark may be added to that bipolar potential waveform. Alternatively, for example, a bipolar potential waveform having a larger peak-to-peak value may be estimated as a formal bipolar potential waveform, and a mark may be added to that bipolar potential waveform.

Bipolar potential waveforms of reference channels to be used to adjust the position of a mark are specified in a certain reference range 51 which is set in advance. As the reference range 51, for example, a certain period in the front-rear direction on the time axis (in FIG. 3, the left-right direction) based on the position of the mark 43 added to the bipolar potential waveform 42 of the main channel 41 is set. In FIG. 3, in the period which is the reference range 51, one bipolar potential waveform of the reference channel A 45 and one bipolar potential waveform of the reference channel B 48 are included. However, the period which is the reference range 51 can be set by automatically measuring excitation intervals on the basis of the potential waveforms, so as to change such that neighboring excitations do not interfere with each other in the same channel.

In the example of FIG. 3, the position of a mark added to the bipolar potential waveform of a main channel can be adjusted to a position having the same phase as that of the temporal average position of the marks added to the bipolar potential waveforms of reference channels. For example, as illustrated in FIG. 3, the position of the mark 43 added to the bipolar potential waveform 42 of the main channel 41 can be moved to the position of a mark 52 which is a position having the same phase as that of the temporal average position of the mark 47 of the bipolar potential waveform 46 of the reference channel A 45 and the mark 50 of the bipolar potential waveform 49 of the reference channel B 48.

Since the period which is the reference range 51 is appropriately set on the basis of excitation intervals based on potential waveforms, individual marks act on each other, and are sequentially and appropriately adjusted without being aligned in one line in the vertical direction.

Figure 4:
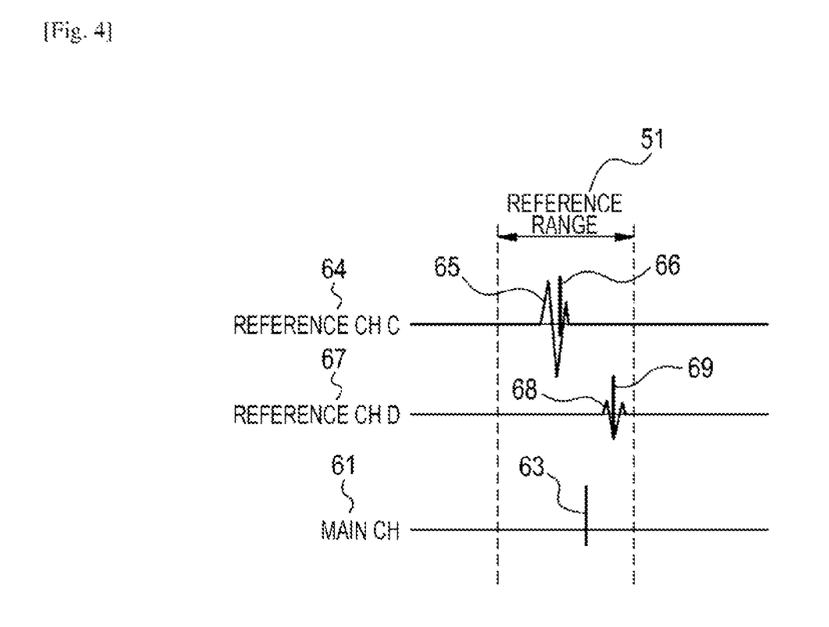
FIG. 4 is a view for explaining mark position correction.

FIG. 4 is a view illustrating an adjustment example of a mark of a main channel in the case where any mark has been added to the main channel since it was impossible to detect a bipolar potential due to a failure in contact of an electrode with a heart wall. In this case, on the basis of marks added to the bipolar potential waveforms of reference channels, the bipolar potential waveform is supplemented with the mark.

As illustrated in FIG. 4, the mark of the bipolar potential waveform of the main channel is added at a position having the same phase as the temporal average position of marks of the bipolar potential waveforms of at least two reference channels. For example, although a bipolar potential waveform does not exist in a main channel 61, a mark 63 is added at a position having the same phase as that of the temporal average position of a mark 66 of a bipolar potential waveform 65 of a reference channel C 64 and a mark 69 of a bipolar potential waveform 68 of a reference channel D 67.

Also, in this case, as the reference range 51, for example, a certain period in the front-rear direction on the time axis (in FIG. 4, the left-right direction) based on the position of the mark 66 added to the bipolar potential waveform 65 of the reference channel C 64 is set. Also, the reference range 51 can be set by automatically measuring excitation intervals on the basis of the potential waveforms, so as to change such that neighboring excitations do not interfere with each other in the same channel.

Adjustment of the position of a mark on a bipolar potential waveform of a main channel as described above is performed on every main channel which is generated by combining two predetermined electrodes. Also, adjustment of the position of a mark which is performed on each main channel is performed sequentially and repeatedly.

Table 2 shows the relation between the main channels and the reference channels. As shown in Table 2, the main channels of the multi-electrode catheter X (see FIG. 2) are 32 channels, i.e. CH 1 to CH 32. This main channels (CH 1 to CH 32) mean CH 1 to CH 32 shown in Table 1. Also, as described above, as reference channels for each main channel, reference channels highly relevant to the corresponding main channel are set. Each reference channel is set by combining two electrodes including one electrode of two electrodes constituting the corresponding main channel.

TABLE 2

| Main Channel | Reference Channel | | | | | |
|---|---|---|---|---|---|---|
| CH 1 | CH 2 | CH 20 | CH 21 | | | |
| CH 2 | CH 1 | CH 3 | CH 21 | CH 22 | | |
| CH 3 | CH 2 | CH 4 | CH 22 | CH 23 | | |
| CH 4 | CH 3 | CH 5 | CH 23 | CH 24 | | |
| CH 5 | CH 4 | CH 6 | CH 24 | CH 25 | | |
| CH 6 | CH 5 | CH 7 | CH 25 | CH 26 | | |
| CH 7 | CH 6 | CH 8 | CH 26 | CH 27 | | |
| CH 8 | CH 7 | CH 9 | CH 27 | CH 28 | | |
| CH 9 | CH 8 | CH 10 | CH 28 | CH 29 | | |
| CH 10 | CH 9 | CH 11 | CH 29 | CH 30 | | |
| CH 11 | CH 10 | CH 12 | CH 30 | CH 31 | | |
| CH 12 | CH 11 | CH 13 | CH 20 | CH 31 | CH 32 | |
| CH 13 | CH 12 | CH 14 | CH 20 | CH 21 | CH 32 | |
| CH 14 | CH 13 | CH 15 | CH 21 | CH 22 | | |
| CH 15 | CH 14 | CH 16 | CH 22 | CH 23 | | |
| CH 16 | CH 15 | CH 17 | CH 23 | CH 24 | CH 25 | CH 26 |
| CH 17 | CH 16 | CH 18 | CH 25 | CH 26 | CH 27 | |
| CH 18 | CH 17 | CH 19 | CH 27 | CH 28 | | |
| CH 19 | CH 18 | CH 28 | CH 29 | CH 30 | CH 31 | CH 32 |
| CH 20 | CH 1 | CH 12 | CH 13 | CH 32 | | |
| CH 21 | CH 1 | CH 2 | CH 13 | CH 14 | | |
| CH 22 | CH 2 | CH 3 | CH 14 | CH 15 | | |
| CH 23 | CH 3 | CH 4 | CH 15 | CH 16 | CH 24 | |
| CH 24 | CH 4 | CH 5 | CH 15 | CH 16 | CH 23 | |
| CH 25 | CH 5 | CH 6 | CH 16 | CH 17 | CH 26 | |
| CH 26 | CH 6 | CH 7 | CH 16 | CH 17 | CH 25 | |
| CH 27 | CH 7 | CH 8 | CH 17 | CH 18 | | |
| CH 28 | CH 8 | CH 9 | CH 18 | CH 19 | | |
| CH 29 | CH 9 | CH 10 | CH 19 | CH 30 | CH 31 | CH 32 |
| CH 30 | CH 10 | CH 11 | CH 19 | CH 29 | CH 31 | CH 32 |
| CH 31 | CH 11 | CH 12 | CH 19 | CH 29 | CH 30 | CH 32 |
| CH 32 | CH 12 | CH 13 | CH 19 | CH 29 | CH 30 | CH 31 |

For example, for CH 1 which is a main channel, three reference channels, i.e. CH 2, CH 20, and CH 21 are set. CH 1 which is a main channel is configured by the electrode 1 and the electrode 2 (see Table 1). Therefore, CH 20 (the electrode 1 and the electrode 13) including the electrode 1 constituting the main channel, i.e. CH 1, and CH 2 (the electrode 2 and the electrode 3) and CH 21 (the electrode 2 and the electrode 14) including the electrode 2 are set as reference channels.

Also, for example, for CH 2 which is a main channel, four reference channels, i.e. CH 1, CH 3, CH 21, and CH 22 are set. This main channel. i.e. CH 2 is configured by the electrode 2 and the electrode 3. Therefore, CH 1 (the electrode 1 and the electrode 2) and CH 21 (the electrode 2 and the electrode 14) including the electrode 2 constituting the main channel, i.e. CH 2, and CH 3 (the electrode 3 and the electrode 4) and CH 22 (the electrode 3 and the electrode 15) including the electrode 3 are set as reference channels.

Figure 5:
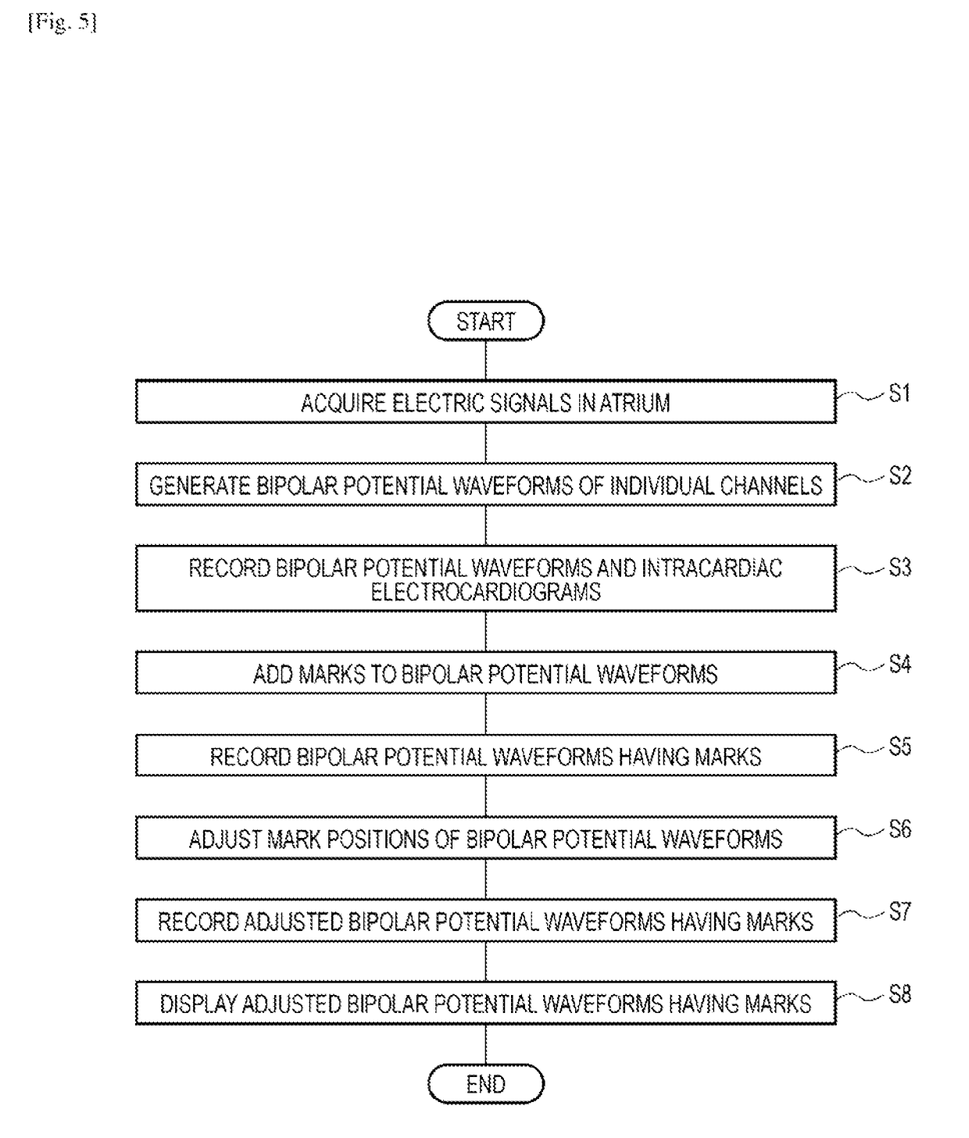
FIG. 5 is a flow chart for explaining the operation of the recording device.

Now, an example of a recording method which is an operation of the recording device 100 will be described with reference to the flow chart illustrated in FIG. 5. Also, a program for performing this recording method is recorded in the above-described recording device 100, and makes it possible to instruct calculating processes for realizing the individual functions.

First of all, the acquisition unit 102 acquires intracardiac ECGs which am vital signs (potentials) in an atrium of a subject through the electrode 1 and the electrode 20 of the multi-electrode catheter X (STEP S1).

Subsequently, the potential calculator 31 of the calculator 103 generates bipolar potential waveforms of CH 1 to CH 32 on the basis of the electric signals of the electrode 1 to the electrode 20 acquired by the acquisition unit 102 (STEP S2). Data on the generated bipolar potential waveforms of CH 1 to CH 32 is recorded in the recording unit 104 (STEP S3).

The addition unit 32 adds marks to the bipolar potential waveforms of CH 1 to CH 32 generated by the potential calculator 31 (STEP S4). For example, the addition unit 32 adds a mark to in the middle between two peaks of each bipolar potential waveform. Data on the bipolar potential waveforms of CH 1 to CH 32 having the marks added thereto is recorded in the recording unit 104 (STEP S5).

The adjusting unit 33 adjusts the set positions of the marks added to the bipolar potential waveforms of the main channels, i.e. CH 1 to CH 32, on the basis of the positions of the marks added to the bipolar potential waveforms of predetermined reference channels (see Table 2) (STEP S6). For example, the adjusting unit 33 specifies the bipolar potential waveforms of reference channels to be used to adjust the position of the mark of the bipolar potential waveform of each main channel, in the reference range 51. The adjusting unit 33 adjusts the position of the mark of the bipolar potential waveform of the corresponding main channel, to a position having the same phase as that of the temporal average position of the marks of the specified bipolar potential waveforms of the reference channels. Data on the bipolar potential waveforms of the main channels. i.e. CH 1 to CH 32 subjected to the mark position adjustment is recorded in the recording unit 104 (STEP S7).

Subsequently, the bipolar potential waveforms of the main channels. i.e. CH 1 to CH 32 subjected to the mark position adjustment are displayed on the display 105 (STEP S8).

Figure 6:
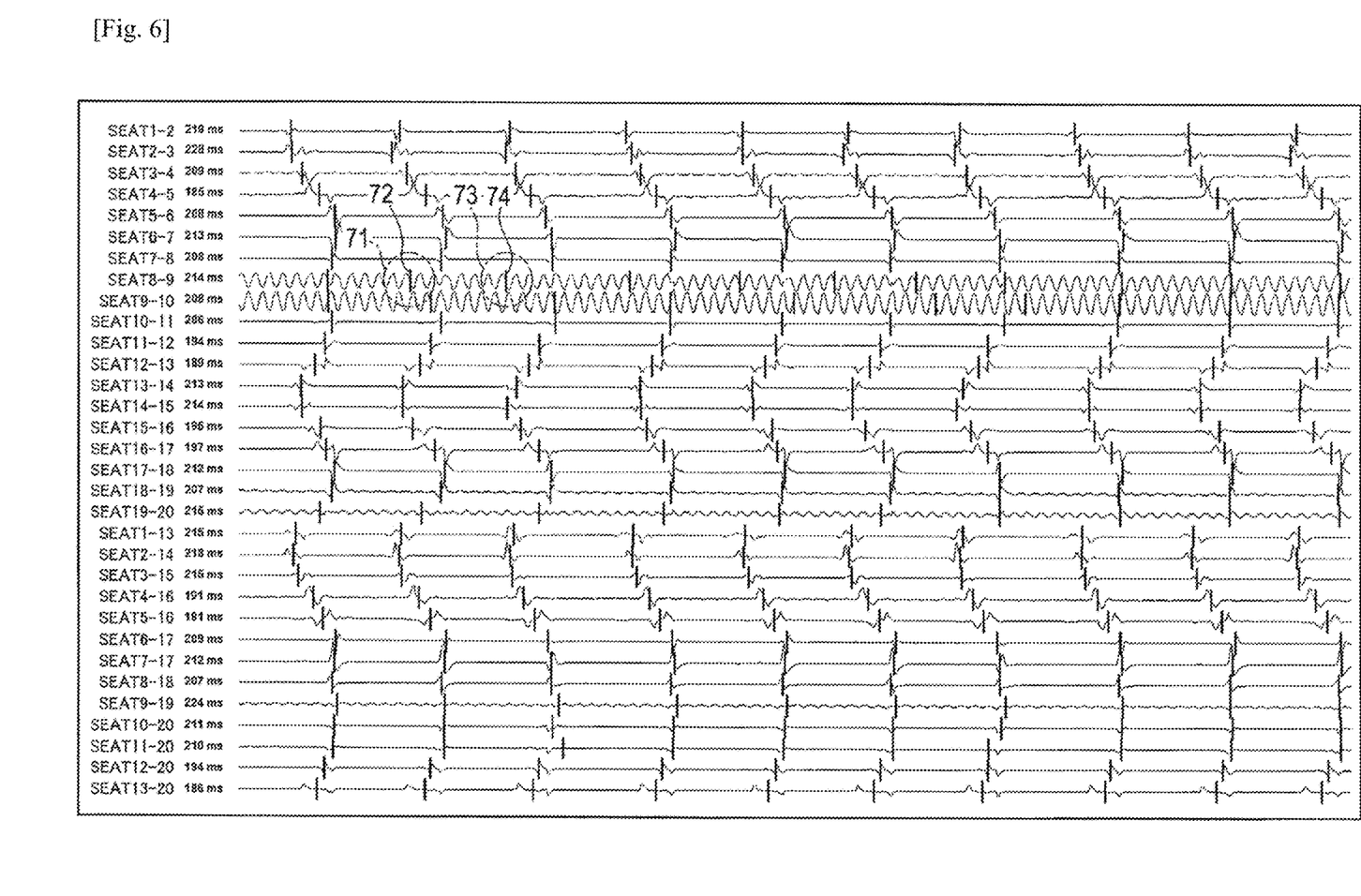
FIG. 6 illustrates an example of bipolar potential waveforms of individual channels.
Figure 7:
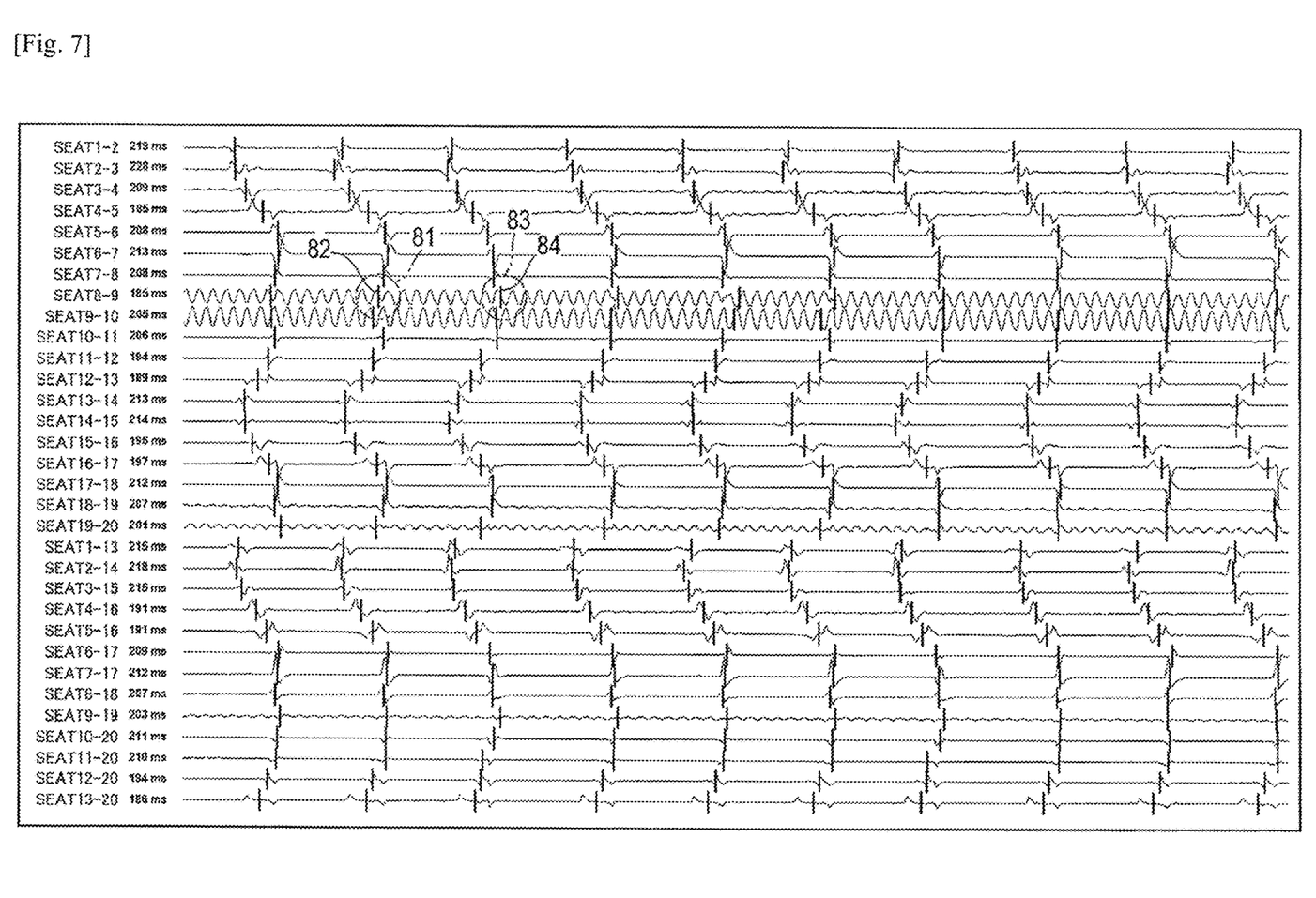
FIG. 7 is a view illustrating the bipolar potential waveforms illustrated in FIG. 6 after mark position adjustment is performed.

FIG. 6 is a view illustrating an image which is obtained in STEP S4 described above before the positions of the marks added to die bipolar potential waveforms of CH 1 to CH 32 are adjusted. FIG. 7 is a view illustrating an image which is obtained in STEP S6 after the positions of the marks of the bipolar potential waveforms of FIG. 6 are adjusted.

For example, in FIG. 6, in a broken line area 71 of the bipolar potential waveform of SEAT 8-9 (CH 8 (the electrode 8 and the electrode 9)), a mark 72 which has not been subjected to position adjustment is added. Similarly or the same, in a broken line area 73, a mark 74 is added. As illustrated in FIG. 6, the bipolar potential waveform of CH 8 has a shape totally different from those of the bipolar potential waveforms of the other channels (for example, the bipolar potential waveforms of SEAT 1-2 to SEAT 7-8). This is considered as being caused since the electrode 8 or the electrode 9 cannot correctly detect the electric signal.

Meanwhile, as illustrated in FIG. 7, in the bipolar potential waveform of CH 8 (the electrode 8 and the electrode 9) subjected to the mark position adjustment, the position of the mark 72 added in the broken line area 71 of FIG. 6 has been adjusted to the position of a mark 82 in a broken line area 81 of FIG. 7. Similarly to or the same, the position of the mark 74 added in the broken line area 73 of FIG. 6 has been moved to the position of a mark 84 in a broken line area 83 of FIG. 7. As described above, the adjustment of the positions of the marks of the main channel. i.e. CH 8 is performed on the basis of the positions of the marks of the bipolar potential waveforms of reference channels highly relevant to CH 8 which is the main channel (having electrodes close to the electrodes of the main channel). i.e. CH 7, CH 9, CH 27, and CH 28.

By the way, the bipolar potential recording method can measure and record the potentials of narrower ranges, as compared to the unipolar potential recording method. Also, the bipolar potential recording method has an advantage that it is unlikely to be influenced by excitations of areas far from the electrodes (far field potentials). Meanwhile, in the bipolar potential recording method, in some cases, such as the case where any one electrode of two unipolar electrodes constituting a bipolar electrode fails in coming into contact with a heart wall due to the roughness of the heart wall, the case where any one electrode of two unipolar electrodes constituting a bipolar electrode is influenced by noise, and the case where the arrangement of two unipolar electrodes constituting a bipolar electrode is perpendicular to the excitation propagation direction, excitations of local spots may not be exactly reflected in bipolar potential waveforms. Therefore, for example, it is required to supplement such parts. In the case of supplementing bipolar potential waveforms, in the related art, for example, the supplementing process is performed in a single channel.

In contrast with this, according to the recording device 100 of the presently disclosed subject matter, in order to adjust the position of a mark of the bipolar potential waveform of a main channel, a plurality of other channels is used as reference channels. To this end, as reference channels which can be used for adjustment, channels including electrodes included in the main channels are defined in advance, such that the bipolar potential waveform of each main channel and the bipolar potential waveforms of reference channels are combined so as to have a desired relevance. Therefore, for example, even if the positions of marks added to the individual bipolar potential waveforms by the addition unit 32 are influenced by noise, the adjusting unit 33 can adjust the positions of the marks, added to the bipolar potential waveforms of the main channels, on the time axis, using the bipolar potential waveforms of the reference channels. As described above, the position of a mark once added to the bipolar potential waveform of a certain channel can be adjusted on the basis of the bipolar potential waveforms of other channels having high relevance, whereby it is possible to improve the accuracy of analysis using the bipolar potential mark distribution chart.

Also, according to the recording device 100, the position of a mark of a main channel can be adjusted on the basis of marks added to the bipolar potential waveforms of reference channels in the predetermined reference range 51. Therefore, it is possible to appropriately select the bipolar potential waveforms of reference channels highly relevant to the bipolar potential waveform of each main channel, and it is possible to improve the accuracy of analysis using the bipolar potential mark distribution chart.

Also, according to the recording device 100, adjustment of the position of a mark of a main channel is performed by moving the position of the mark of the main channel to the temporal average position of marks of reference channels. Therefore, it is possible to adjust the position of a mark to the average position of marks added to bipolar potential waveforms having high relevance. Moreover, it is possible to improve the accuracy of analysis using the bipolar potential mark distribution chart.

Also, according to the recording device 100, if any mark is added to a main channel in the reference range 51, to the bipolar potential waveform of the main channel, a mark is added at a position having the same phase as that of the temporal average position of marks added to the bipolar potential waveforms of reference channels. Therefore, even in the case where it is impossible to sufficiently detect the waveform (excitation) of a main channel, such as the case where an electrode does not abut on an atrium, it is possible to perform effective processing.

Also, according to the recording device 100, the process of adjusting the positions of marks repeatedly performs positive adjustment. Therefore, since adjustment is repeated on the basis of marks added to bipolar potential waveforms having high relevance, it is possible to further improve the accuracy of analysis using the bipolar potential mark distribution chart.

In the above-described embodiment, the case of inserting the sensor device into the heart of a subject and detecting intracardiac ECGs has been described; however, the presently disclosed subject matter is not limited to this embodiment. The presently disclosed subject matter can be applied to other cases such as the cases of bringing a sensor device into contact with the epicardium side of the heart of a subject or inspecting a muscle or a brain.

Also, since the essence of the presently disclosed subject matter is the technique for temporarily and spatially supplementing vital signs using reference channels relevant to main channels, not complementing only main channels for vital signs, the embodiment is not limited to the above-described configuration, and various modifications, improvements, etc. can be made as appropriate. Also, the materials, shapes, dimensions, numeric values, modes, numbers and installation places, and so on of the individual components of the above-described embodiment are optional and are not limited as long as it is possible to implement the presently disclosed subject matter.

CROSS-REFERENCE TO RELATED APPLICATION

This application is based upon and claims the benefit of priority from Japanese Patent Application No. 2019-011333 filed on Jan. 25, 2019.

The invention claimed is:

1. A recording device comprising:
at least one processor configured to
acquire vital signs through a sensor device having a plurality of electrodes;
record a bipolar potential of a main channel, the main channel defined by combining two electrodes of the plurality of electrodes;
add a mark to each bipolar potential waveform at a predetermined position on a time axis; and
adjust a position of the mark added to each bipolar potential waveform,
wherein the adjusting comprises adjusting the position of each mark added to the bipolar potential waveform within a predetermined reference range based on bipolar potentials of reference channels, wherein each of the reference channels include at least one of the electrodes included in the main channel.

2. The recording device according to claim 1, wherein
a number of the reference channels is at least two, and
the adjusting further comprises moving the position of the mark added to the bipolar potential of the main channel, to a temporal average position of marks included in the at least two reference channels.

3. The recording device according to claim 1, wherein
a number of the reference channels is at least two, and
in a case where no mark is added to the main channel in the predetermined reference range, the adjusting further comprises adding a mark to the bipolar potential of the main channel, at a temporal average position of marks of the at least two reference channels.

4. The recording device according to claim 1, wherein
the adjusting comprises sequentially and repeatedly adjusting the position of the mark added to the bipolar potential of the main channel.

5. A recording method comprising:
acquiring vital signs through a sensor device having a plurality of electrodes;
recording a bipolar potential of a main channel, the main channel defined by combining two electrodes of the plurality of electrodes;
adding a mark to each bipolar potential waveform at a predetermined position on the time axis; and
first adjusting a position of the mark added to each bipolar potential waveform,
wherein the first adjusting the position of each mark added to the bipolar potential waveform within a predetermined reference range based on bipolar potentials of reference channels, wherein each of the reference channels include at least one of the electrodes included in the main.

6. The recording method according to claim 5, wherein
a number of the reference channels is at least two, and
the first adjusting comprises moving the position of the mark added to the bipolar potential of the main channel, to a temporal average position of marks included in the at least two reference channels.

7. The recording method according to claim 5, wherein
a number of the reference channels is at least two, and
in a case where no mark is added to the main channel in the predetermined reference range, the first adjusting comprises adding a mark to the bipolar potential of the main channel, at a temporal average position of marks of the at least two reference channels.

8. The recording method according to claim 5, wherein
the first adjusting comprises sequentially and repeatedly performing a process of adjusting the position of the mark added to the bipolar potential of the main channel.

9. A non-transitory computer-readable recording medium storing a computer program for making a computer to execute a process, the process comprising:
acquiring vital signs through a sensor device having a plurality of electrodes;
recording a bipolar potential of a main channel, the main channel defined by combining the plurality of electrodes;
adding a mark to each bipolar potential waveform at a predetermined position on the time axis; and
adjusting a position of the mark added to each bipolar potential waveform,
wherein the adjusting comprises the position of each mark added to the bipolar potential waveform within a predetermined reference range based on bipolar potentials of reference channels, wherein each of the reference channels include at least one of the including electrodes included in the main channel.

* * * * *